United States Patent [19]
Guthrie

[11] Patent Number: 5,262,318
[45] Date of Patent: Nov. 16, 1993

[54] ISOLATED DNA ENCODING THE SPHI RESTRICTION ENDONUCLEASE AND RELATED METHODS FOR PRODUCING THE SAME

[75] Inventor: Ellen P. Guthrie, Andover, Mass.

[73] Assignee: New England Biolabs, Inc., Beverly, Mass.

[21] Appl. No.: 932,454

[22] Filed: Aug. 20, 1992

[51] Int. Cl.$^5$ .............. C12N 9/22; C12N 15/55
[52] U.S. Cl. .................. 435/199; 435/320.1; 435/252.33; 435/252.35; 435/193; 536/23.2
[58] Field of Search ........... 435/199, 193, 320.1, 435/252.33, 252.35; 536/23.2

[56] References Cited

FOREIGN PATENT DOCUMENTS 0193413 9/1986 European Pat. Off. .

OTHER PUBLICATIONS

Kosykh et al., Molec. Gen. Genet., 178:717–718 (1980).
Mann et al., Gene, 3:97–112 (1978).
Walder et al., Proc. Natl. Acad. Sci. USA, 78:1503–1507 (1981).
Bougueleret et al., Nucleic Acids Research, 12:3659–3676 (1984).
Gingeras and Brooks, Proc. Natl. Acad. Sci. USA 80:402–406 (1983).
Theriault & Roy, Gene, 19:355–359 (1982).
Blumenthal et al., J. Bacteriol., 164:501–509 (1985).
Szomolanyi et al., Gene, 10:219–225 (1980).
Janulaitis et al., Gene, 20:197–204 (1982).
Kiss & Baldauf, Gene, 21:111–119 (1983).
Walder et al., J. Biol. Chem., 258:1235–1241 (1983).
Raleigh & Wilson, Proc. Natl. Acad. Sci. USA, 83:9070–9074 (1986).
Ward et al., Mol. Gen. Genet., 203:468–478 (1986).
Kiss et al., Nucleic Acids Research, 13:6403–6421 (1985).
Fuchs et al., Gene, 10:39–46 (1980).
Bernan et al., ASM Abstracts 89:206 (1989).
Brooks et al., J. Cell. Biochem. Supplemental 14A:106 (1990).
Rodico & Chater, Mol. Gen. Genet., 213:346–353 (1988).

*Primary Examiner*—Charles L. Patterson, Jr.
*Attorney, Agent, or Firm*—Gregory D. Williams; David G. Conlin

[57] ABSTRACT

The present invention is directed to a method for cloning and producing the SphI restriction endonuclease by 1) introducing the restriction endonuclease gene from *Streptomyces phaeochromogenes* into a host whereby the restriction gene is expressed; 2) fermenting the host which contains the plasmid encoding and expressing the SphI restriction endonuclease activity, and 3) purifying the SphI restriction endonuclease from the fermented host which contains the plasmid encoding and expressing the SphI restriction endonuclease activity.

7 Claims, 5 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 235 amino acids
( B ) TYPE: amino acid
( D ) TOPOLOGY: linear ( i i ) MOLECULE TYPE: protein ( x i ) SEQUENCE DESCRIPTION: SEQ ID NO:1:

| Met | Thr | Ser | Lys | Asp | Pro | Ile | Val | Leu | Ser | Ala | Asp | Gln | Ile | Ala | Trp |
|---|---|---|---|---|---|---|---|---|---|---|---|---|---|---|---|
| 1 | | | | 5 | | | | | 10 | | | | | 15 | |

| Leu | Arg | Gln | Leu | Lys | Met | Ser | Lys | Arg | Ala | Ala | Leu | Val | Arg | Asp | Tyr |
|---|---|---|---|---|---|---|---|---|---|---|---|---|---|---|---|
| | | | 20 | | | | 25 | | | | | 30 | | | |

| Ile | Leu | Glu | Tyr | Gly | Ala | Val | Thr | Thr | Gly | Lys | Leu | Ala | Glu | Leu | Gly |
|---|---|---|---|---|---|---|---|---|---|---|---|---|---|---|---|
| | | 35 | | | | | 40 | | | | | 45 | | | |

| Tyr | Ser | His | Pro | Pro | Arg | Ala | Ala | Arg | Asp | Leu | Lys | Asp | Ala | Gly | Ala |
|---|---|---|---|---|---|---|---|---|---|---|---|---|---|---|---|
| | 50 | | | | | 55 | | | | | 60 | | | | |

| Gly | Val | Val | Thr | Ile | Met | Val | Lys | Gly | Pro | Asp | Gly | Arg | Arg | Met | Ala |
|---|---|---|---|---|---|---|---|---|---|---|---|---|---|---|---|
| 65 | | | | | 70 | | | | | 75 | | | | | 80 |

| Ser | Tyr | Ala | Phe | Asn | Gly | Lys | Ala | Asn | Glu | Asp | Gly | Ala | Gly | Arg | Val |
|---|---|---|---|---|---|---|---|---|---|---|---|---|---|---|---|
| | | | | 85 | | | | | 90 | | | | | 95 | |

| Val | Ile | Pro | Lys | Ala | Phe | Gly | Glu | Ala | Leu | Lys | Arg | Ala | His | Gly | Gly |
|---|---|---|---|---|---|---|---|---|---|---|---|---|---|---|---|
| | | | 100 | | | | | 105 | | | | | 110 | | |

| Lys | Cys | Ala | Val | Cys | Tyr | Gly | Asp | Phe | Ser | Glu | Arg | Glu | Leu | Gln | Cys |
|---|---|---|---|---|---|---|---|---|---|---|---|---|---|---|---|
| | | 115 | | | | | 120 | | | | | 125 | | | |

| Asp | His | Arg | Val | Pro | Phe | Ala | Ile | Ala | Gly | Asp | Lys | Pro | Lys | Leu | Val |
|---|---|---|---|---|---|---|---|---|---|---|---|---|---|---|---|
| | 130 | | | | | 135 | | | | | 140 | | | | |

| Gln | Glu | Asp | Phe | Met | Pro | Leu | Cys | Ala | Ser | Asp | Asn | Arg | Ala | Lys | Ser |
|---|---|---|---|---|---|---|---|---|---|---|---|---|---|---|---|
| 145 | | | | | 150 | | | | | 155 | | | | | 160 |

| Trp | Ser | Cys | Glu | Asn | Cys | Pro | Asn | Trp | Glu | Leu | Lys | Asp | Glu | Asp | Thr |
|---|---|---|---|---|---|---|---|---|---|---|---|---|---|---|---|
| | | | | 165 | | | | | 170 | | | | | 175 | |

| Cys | Arg | Ser | Cys | Phe | Trp | Ala | Ser | Pro | Glu | Asn | Tyr | Thr | His | Val | Ser |
|---|---|---|---|---|---|---|---|---|---|---|---|---|---|---|---|
| | | | 180 | | | | | 185 | | | | | 190 | | |

| Thr | Arg | Pro | Glu | Arg | Arg | Ile | Asn | Leu | Leu | Phe | Gln | Gly | Asp | Glu | Val |
|---|---|---|---|---|---|---|---|---|---|---|---|---|---|---|---|
| | | 195 | | | | | 200 | | | | | 205 | | | |

| Glu | Ile | Phe | Asp | Ala | Leu | Lys | Asn | Ala | Ala | Ala | Asn | Glu | Gly | Val | Ser |
|---|---|---|---|---|---|---|---|---|---|---|---|---|---|---|---|
| | 210 | | | | | 215 | | | | | 220 | | | | |

| Leu | Thr | Glu | Ala | Thr | Lys | Arg | Lys | Leu | Ala | Asp |
|---|---|---|---|---|---|---|---|---|---|---|
| 225 | | | | | 230 | | | | | 235 |

( 2 ) INFORMATION FOR SEQ ID NO:2:

( i ) SEQUENCE CHARACTERISTICS:
  ( A ) LENGTH: 2692 base pairs
  ( B ) TYPE: nucleic acid
  ( C ) STRANDEDNESS: double
  ( D ) TOPOLOGY: linear ( i x ) FEATURE:
  ( A ) NAME/KEY: CDS
  ( B ) LOCATION: 703..1653
  ( D ) OTHER INFORMATION: /note="METHYLASE GENE STARTS AT
   POSITION 703/ENDS AT 1653. RESTRICTION
   ENDONUCLEASE STARTS AT POSITION 1703/ENDS AT 2410"

( i x ) FEATURE:
  ( A ) NAME/KEY: CDS
  ( B ) LOCATION: 1703..2410

( x i ) SEQUENCE DESCRIPTION: SEQ ID NO:2:

```
GCGCGCGAGG  TGCGGAAGTC  GCGCTCCTCG  GCGGCGAGGA  CGGCCTGCCG  GACGGTGAGC      60

GGGATCTGGT  CGAGGCGGAC  GTTCTCGCGG  TTGACCTCGC  CGTCGCGGGC  GAGGGGGGTG     120

CCGTCCCGGT  AGAGGTAGAC  GTTGGACTGG  GCGACGGCGG  CGGCGTTGGC  GGGCGGGATC     180

TCCACCAGGA  GGTAGCCGGC  GGCGAAGGCA  CCCGCGCTCA  GCAGCATGCC  GAGCAGGAGG     240

AGCCCGAGGA  GGGTGCGCAG  GACGCGACGG  GGGCGTCGGC  GCCTCTCCAC  CGGGCCGGGA     300

AGGGTGGGGT  CCCTCGGCTC  CCAGCCGTCC  GGGTGGGGGT  CGTCGTCGCT  CGTACCGCTC     360
```

| | | | | | | | | | | |
|---|---|---|---|---|---|---|---|---|---|---|
| GTACTGGAGG | AAGGGGACAT | GGCATCACAT | ACTGCATGGA | ATCGGTGGAA | ACTCCCCCGA | | | | | 420 |
| CCGACCCGAG | GGTGGCGCGA | AAACGGCGCG | GGGTGGGCGG | GGTGGGGCCG | GGACCCGGGT | | | | | 480 |
| CGGTGCGGGT | GCTGCCGGGG | TCGTGCTCTG | CCTGCTGCCG | CGCGGAACCT | TGCGAACGGT | | | | | 540 |
| GAGGTTCATA | CGGCGCGAAC | CGGATCGGTG | AAATAAGATT | CGCCGCTTTA | ATCGCACGGG | | | | | 600 |
| CGGAATTGAC | GGAAGGGGAA | CGTCCAATAC | TGCCGAAGTA | AGGGATTCCG | AGGGACTCCC | | | | | 660 |
| CGAATCAGGT | AGACTGTGCC | GGTGAGCGTT | GTCGATGATC | CC ATG AAT GAC CGG | | | | | | 714 |
| | | | | Met Asn Asp Arg | | | | | | |
| | | | | 1 | | | | | | |

| | | | | | | | | | | | | | | | | |
|---|---|---|---|---|---|---|---|---|---|---|---|---|---|---|---|---|
| ATG | CCC | TGG | AAG | GCT | GCC | GGT | ATC | CGG | AGT | GTC | CCG | CAG | GCA | TTT | CCG | 762 |
| Met | Pro | Trp | Lys | Ala | Ala | Gly | Ile | Arg | Ser | Val | Pro | Gln | Ala | Phe | Pro | |
| 5 | | | | 10 | | | | | 15 | | | | | | 20 | |
| TAT | CAG | GGC | AGC | AAG | CGA | GCG | CTT | GCC | AGC | CAG | ATT | CTT | TCT | CTC | TTC | 810 |
| Tyr | Gln | Gly | Ser | Lys | Arg | Ala | Leu | Ala | Ser | Gln | Ile | Leu | Ser | Leu | Phe | |
| | | | | 25 | | | | | 30 | | | | | 35 | | |
| CCG | CAT | GGC | GGA | GTG | CCT | CGT | CTC | GTG | GAG | CCG | TTC | GCC | GGC | TCG | GCG | 858 |
| Pro | His | Gly | Gly | Val | Pro | Arg | Leu | Val | Glu | Pro | Phe | Ala | Gly | Ser | Ala | |
| | | | 40 | | | | | 45 | | | | | 50 | | | |
| GCC | ATC | TCT | GTC | GCG | GCG | CGC | CAC | TAC | GGA | ATC | GCG | GAG | ACG | GCT | CTC | 906 |
| Ala | Ile | Ser | Val | Ala | Ala | Arg | His | Tyr | Gly | Ile | Ala | Glu | Thr | Ala | Leu | |
| | | 55 | | | | | 60 | | | | | 65 | | | | |
| ATT | TCG | GAC | GTC | AAC | GAG | CCG | CTC | ATG | GGG | CTG | TGG | AAG | CTC | ATC | ATC | 954 |
| Ile | Ser | Asp | Val | Asn | Glu | Pro | Leu | Met | Gly | Leu | Trp | Lys | Leu | Ile | Ile | |
| | 70 | | | | | 75 | | | | | 80 | | | | | |
| GAG | GAC | CCG | CGG | CAT | CTG | ATC | GCC | GAG | TAC | ACC | CGC | TTG | TGG | AAC | GAA | 1002 |
| Glu | Asp | Pro | Arg | His | Leu | Ile | Ala | Glu | Tyr | Thr | Arg | Leu | Trp | Asn | Glu | |
| 85 | | | | | 90 | | | | | 95 | | | | | 100 | |
| CAG | CTG | GAT | GAC | CCT | CGC | GCG | TAC | TTC | CTG | GAA | GCT | CGC | GAC | AAG | TTC | 1050 |
| Gln | Leu | Asp | Asp | Pro | Arg | Ala | Tyr | Phe | Leu | Glu | Ala | Arg | Asp | Lys | Phe | |
| | | | | 105 | | | | | 110 | | | | | 115 | | |
| AAC | GCC | ACG | AAG | CAG | CCG | GAA | ATC | CTG | CTC | TAC | CTT | CTG | TGC | CGT | TGC | 1098 |
| Asn | Ala | Thr | Lys | Gln | Pro | Glu | Ile | Leu | Leu | Tyr | Leu | Leu | Cys | Arg | Cys | |
| | | | 120 | | | | | 125 | | | | | 130 | | | |
| GTA | AAG | GCC | GCC | GTC | CGC | TAC | AGC | CAG | AAG | ACC | GGC | GAT | TTC | AAC | CAG | 1146 |
| Val | Lys | Ala | Ala | Val | Arg | Tyr | Ser | Gln | Lys | Thr | Gly | Asp | Phe | Asn | Gln | |
| | | 135 | | | | | 140 | | | | | 145 | | | | |
| GGC | GCC | GAC | CAC | CGC | CGC | CTC | GGA | GCG | AAT | CCG | GCG | AAC | ATG | GCG | GAG | 1194 |
| Gly | Ala | Asp | His | Arg | Arg | Leu | Gly | Ala | Asn | Pro | Ala | Asn | Met | Ala | Glu | |
| | 150 | | | | | 155 | | | | | 160 | | | | | |
| CGC | ATC | GGC | CGG | GCT | TCC | GCC | ATC | ATG | CAG | GGC | GTG | ACC | GTG | TCC | ACC | 1242 |
| Arg | Ile | Gly | Arg | Ala | Ser | Ala | Ile | Met | Gln | Gly | Val | Thr | Val | Ser | Thr | |
| 165 | | | | | 170 | | | | | 175 | | | | | 180 | |
| TCG | ACG | TAC | GAG | GAC | GCG | CTG | GTC | AAT | GCC | GCA | CCC | GAT | GAA | CTC | GTC | 1290 |
| Ser | Thr | Tyr | Glu | Asp | Ala | Leu | Val | Asn | Ala | Ala | Pro | Asp | Glu | Leu | Val | |
| | | | | 185 | | | | | 190 | | | | | 195 | | |
| TAC | ATG | GAT | CCG | CCG | TAC | CAG | GGG | ACG | AGC | GGC | GTG | CCC | GAC | CAC | CGC | 1338 |
| Tyr | Met | Asp | Pro | Pro | Tyr | Gln | Gly | Thr | Ser | Gly | Val | Pro | Asp | His | Arg | |
| | | | 200 | | | | | 205 | | | | | 210 | | | |
| TAT | CTC | AAG | GGT | CTG | CAG | CGC | GAG | CCC | TTC | GCG | GAA | GTG | CTC | CAG | CAG | 1386 |
| Tyr | Leu | Lys | Gly | Leu | Gln | Arg | Glu | Pro | Phe | Ala | Glu | Val | Leu | Gln | Gln | |
| | | 215 | | | | | 220 | | | | | 225 | | | | |
| GCG | GTG | GAC | AAC | AAA | GTG | TCT | TTC | GTC | GTC | TCG | TAC | GAC | GCG | GTG | ACC | 1434 |
| Ala | Val | Asp | Asn | Lys | Val | Ser | Phe | Val | Val | Ser | Tyr | Asp | Ala | Val | Thr | |
| | 230 | | | | | 235 | | | | | 240 | | | | | |
| GAC | GAC | AAC | AAG | TAC | GGG | TAC | GCC | CTG | CCG | GAG | GAG | CTG | GGG | CTG | ACC | 1482 |
| Asp | Asp | Asn | Lys | Tyr | Gly | Tyr | Ala | Leu | Pro | Glu | Glu | Leu | Gly | Leu | Thr | |
| 245 | | | | 250 | | | | | 255 | | | | | 260 | | |
| CAC | CGC | CAC | GTG | GTC | GCG | GGC | GTC | TCG | GCG | CAG | GCG | ACG | CTC | ATG | GGC | 1530 |
| His | Arg | His | Val | Val | Ala | Gly | Val | Ser | Ala | Gln | Ala | Thr | Leu | Met | Gly | |

```
                   265                            270                            275
AAG AAG CAG ATG ACC ACC GAG TCC CTG TAC ATC TCG CCG GCT CTC GTG              1578
Lys Lys Gln Met Thr Thr Glu Ser Leu Tyr Ile Ser Pro Ala Leu Val
            280                     285                     290

GAG CGC CTC GGG GGT GTC GAC GCG ATC GAC AAG CGA CTC GAT CTG ACA              1626
Glu Arg Leu Gly Gly Val Asp Ala Ile Asp Lys Arg Leu Asp Leu Thr
        295                     300                     305

TCT TCT GCT CAA GAA TCG CTT TTT TAGCCTTTCC GGCAAGACGG GTCGGCTCGA             1680
Ser Ser Ala Gln Glu Ser Leu Phe
        310                 315

TTCCTTCGAC TATAGTGAAG GA ATG ACA AGT AAA GAT CCG ATT GTG CTC TCC             1732
                         Met Thr Ser Lys Asp Pro Ile Val Leu Ser
                          1               5                  10

GCC GAC CAG ATC GCT TGG CTT CGG CAG CTC AAG ATG TCC AAG CGC GCC              1780
Ala Asp Gln Ile Ala Trp Leu Arg Gln Leu Lys Met Ser Lys Arg Ala
                    15                  20                  25

GCC TTG GTG CGG GAT TAC ATT CTT GAA TAC GGC GCC GTC ACC ACG GGC              1828
Ala Leu Val Arg Asp Tyr Ile Leu Glu Tyr Gly Ala Val Thr Thr Gly
                30                  35                  40

AAA CTC GCC GAA CTG GGC TAC AGC CAC CCT CCA CGT GCG GCG CGC GAC              1876
Lys Leu Ala Glu Leu Gly Tyr Ser His Pro Pro Arg Ala Ala Arg Asp
            45                  50                  55

CTG AAG GAC GCG GGA GCC GGG GTC GTC ACC ATC ATG GTC AAG GGC CCG              1924
Leu Lys Asp Ala Gly Ala Gly Val Val Thr Ile Met Val Lys Gly Pro
        60                  65                  70

GAC GGT CGC CGC ATG GCC AGC TAC GCC TTC AAC GGA AAA GCC AAT GAA              1972
Asp Gly Arg Arg Met Ala Ser Tyr Ala Phe Asn Gly Lys Ala Asn Glu
75                  80                  85                  90

GAC GGC GCG GGG CGG GTG GTC ATA CCC AAG GCA TTC GGT GAA GCC TTG              2020
Asp Gly Ala Gly Arg Val Val Ile Pro Lys Ala Phe Gly Glu Ala Leu
                95                  100                 105

AAG AGG GCT CAT GGT GGT AAA TGC GCC GTC TGC TAC GGA GAC TTC TCC              2068
Lys Arg Ala His Gly Gly Lys Cys Ala Val Cys Tyr Gly Asp Phe Ser
            110                 115                 120

GAA CGC GAA CTC CAG TGC GAC CAT CGT GTC CCG TTC GCC ATA GCA GGC              2116
Glu Arg Glu Leu Gln Cys Asp His Arg Val Pro Phe Ala Ile Ala Gly
        125                 130                 135

GAC AAG CCG AAA CTT GTC CAA GAA GAC TTC ATG CCG CTG TGC GCC TCG              2164
Asp Lys Pro Lys Leu Val Gln Glu Asp Phe Met Pro Leu Cys Ala Ser
    140                 145                 150

GAC AAC CGC GCG AAA TCC TGG TCC TGC GAG AAC TGC CCC AAC TGG GAA              2212
Asp Asn Arg Ala Lys Ser Trp Ser Cys Glu Asn Cys Pro Asn Trp Glu
155                 160                 165                 170

TTG AAG GAC GAG GAC ACC TGC AGG TCC TGC TTC TGG GCT TCC CCG GAA              2260
Leu Lys Asp Glu Asp Thr Cys Arg Ser Cys Phe Trp Ala Ser Pro Glu
                175                 180                 185

AAC TAC ACC CAT GTC TCG ACC CGC CCG GAA CGA CGC ATC AAC CTC CTG              2308
Asn Tyr Thr His Val Ser Thr Arg Pro Glu Arg Arg Ile Asn Leu Leu
            190                 195                 200

TTC CAG GGC GAT GAG GTC GAA ATC TTC GAT GCG CTC AAG AAC GCG GCA              2356
Phe Gln Gly Asp Glu Val Glu Ile Phe Asp Ala Leu Lys Asn Ala Ala
        205                 210                 215

GCC AAC GAG GGC GTA TCG CTC ACC GAG GCG ACG AAG CGC AAG CTG GCG              2404
Ala Asn Glu Gly Val Ser Leu Thr Glu Ala Thr Lys Arg Lys Leu Ala
    220                 225                 230

GAC TGAGTCGGCG GCCGGCCGCG TACCCCTGCT CGACCTCTCG GTGCGGGAGC                   2457
Asp

235

CGGACATCGA GGCGGCGATC GCGAAGATGG ACGGGGGAAC TCGGGAGGAT CGCCGGGAGT            2517
```

| CCCTGATGTA | GGGGGACGGA | GGAGGTCGAG | TCGATGGTGA | GTTTCTCGTA | CACGGCGGCG | 2577 |
| GACGAGGAGA | AGAGCAGAGG | CGTCCGCCGC | ATGAAGGCG | TGGCGACGGC | ACTGCTGGCG | 2637 |
| CTGGTGGCCG | TGGTCTACGC | CTGGCACCTG | GGCGCGGAAC | GAGGGCTGGG | GCGCC | 2692 |

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (xi) SEQUENCE DESCRIPTION: SEQ ID NO:3:

CGCATCAGGC GCCGTCACCA CGGGC         25

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (xi) SEQUENCE DESCRIPTION: SEQ ID NO:4:

CCTTCGACTA TAGTGAAGTC ATGACAAG         28

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (xi) SEQUENCE DESCRIPTION: SEQ ID NO:5:

GCGCAGCCTG AATGAAGCTT GGCGCC         26

ISOLATED DNA ENCODING THE SPHI RESTRICTION ENDONUCLEASE AND RELATED METHODS FOR PRODUCING THE SAME

BACKGROUND OF THE INVENTION

The present invention relates to recombinant DNA which encodes the SphI restriction endonuclease and modification methylase, and the production of these enzymes from the recombinant DNA.

Restriction endonucleases are a class of enzymes that occur naturally in bacteria. When they are purified away from other contaminating bacterial components, restriction endonucleases can be used in the laboratory to cut DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Close to one hundred different restriction endonucleases have been identified among the many hundreds of bacterial species that have been examined to date.

Bacteria tend to possess at most, only a small number restriction endonucleases per species. The endonucleases typically are named according to the bacteria from which they are derived. Thus, the species *Haemophilus aegyptius* for example, synthesizes three different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The cleavage that takes place disables many of the infecting genes and renders the DNA susceptible to further degradation by nonspecific endonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., Molec. gen. Genet 178: 717–719, (1980); HhaII: Mann et al., Gene 3: 97–112, (1978); PstI: Walder et al., Proc. Nat. Acad. Sci. 78 1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12: 3659–3676, (1984); PaeR7: Gingeras and Brooks, Proc. Natl. Acad. Sci. USA 80: 402–406, (1983); Theriault and Roy, Gene 19: 355–359 (1982); PvuII: Blumenthal et al., J. Bacteriol. 164: 501–509, (1985)).

A third approach, and one that is being used to clone a growing number of systems are now being cloned by selection for an active methylase gene (See e.g., EPO No.: 193,413 published Sep. 3, 1986 and BsuRI: Kiss et al., Nucl. Acid. Res. 13: 6403–6421, (1985)). Since restriction and modification genes are often closely linked, both genes can often be cloned simultaneously. This selection does not always yield a complete restriction system however, but instead yields only the methylase gene (BspRI: Szomolanyi et al., Gene 10: 219–225, (1980); BcnI: Janulaitis et al, Gene 20: 197–204 (1982); BsuRI: Kiss and Baldauf, Gene 21: 111–119, (1983); and MspI: Walder et al., J. Biol. Chem. 258: 1235–1241, (1983)).

In some systems the cloning problem may lie in trying to introduce the endonuclease gene into a host not already protected by modification. If the methylase gene and endonuclease gene are introduced on a common DNA fragment, the methylase gene must modify or protect the host before the endonuclease gene cleaves the host's genome.

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, Proc. Natl. Acad Sci., USA 83: 9070–9074, (1986)). Therefore, it is also necessary to carefully consider which E. coli strain(s) to use for cloning.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA encoding the genes for the SphI restriction endonuclease and modification methylase obtainable from *Streptomyces phaeochromogenes* (NRRL B-3559) as well as related methods for the production of these enzymes from the recombinant DNA. This invention also relates to a transformed host which expresses the restriction endonuclease SphI, an enzyme which recognizes the DNA sequence 5'-GCATGC-3' and cleaves in the recognition sequence between the second GC pair leaving a 4 base 3' overhang (Fuchs, L. Y., L. Corvarrubias, l. Escalante, S. Sanchez, and F. Bolivar, Gene 10: 39–46, (1980)). SphI restriction endonuclease produced in accordance with the present invention is substantially pure and free of the contaminants normally found in restriction endonuclease preparations made by conventional techniques as described in step 13 of example 1. One preferred method for cloning the SphI restriction-modification system comprises: selecting an appropriate vector, forming several libraries containing DNA from *Streptomyces phaeochromogenes*, isolating those clones which contain DNA coding for the SphI modification methylase, determining whether or not the endonuclease gene is present by assaying for endonuclease activity in strains of E. coli and *Streptomyces lividans* containing the methylase clone, sequencing the cloned DNA and the amino terminus of the SphI restriction endonuclease when the restriction endonuclease was not detected by the refrenced assay, localizing the endonuclease gene on the cloned DNA fragment by comparing these sequences, cloning the chromosomal DNA containing the remainder of the endonuclease gene using southern analysis to screen libraries for the clone, using PCR to amplify the remainder of the endonuclease gene from these libraries, reconstructing the intact endonuclease gene, cloning the intact endonuclease gene behind a regulated promoter, and transforming this into a host which had been preprotected with NlaIII methylase gene on a medium copy number plasmid.

DETAILED DESCRIPTION OF THE INVENTION

The present invention relates to recombinant DNA which encodes the SphI restriction endonuclease, as well as to the enzyme produced from such a recombinant DNA.

The cloning of the SphI restriction endonuclease gene from *Streptomyces phaeochromogenes* proved to be unusually difficult. None of the methylase clones obtained by the usual methylase selection procedure contained the entire restriction endonuclease gene. To locate the restriction endonuclease it was necessary to compare the sequences of the DNA from the methylase clones and the amino terminal sequence obtained from purified SphI restriction endonuclease. From these results it was estimated that approximately 200-400 bp needed to be cloned to obtain the entire restriction-modification system. However all attempts to clone the intact restriction endonuclease by conventional methods proved to be unsuccessful, possibly due to the lethality of the endonuclease gene and the relatively low expression of the SphI methylase gene. The methods tried include: cloning the intact restriction modification system in *E. coli* as well as in *Streptomyces lividans*, and cloning the restriction endonuclease gene into *E. coli* or *S. lividans* preprotected with the SphI methylase. The 3' portion of the restriction endonuclease gene was finally cloned by constructing a KasI library of *S. phaeochromogenes* genomic DNA (KasI cleaves within the restriction endonuclease gene and downstream of the 3' end of the gene). The correct fragment, isolated from the library by amplifying the fragment using PCR, was cloned into pUC19. Primers used for the PCR reaction contained a sequence within the restriction endonuclease gene and within the vector used to construct the library. Once cloned, all attempts to reconstruct the restriction endonuclease gene in *S. lividans* which had been preprotected with SphI methylase under control of its own endogenous promoter on a low copy plasmid, were unsuccessful. The intact restriction endonuclease gene was finally cloned and expressed in *E. coli* by reconstructing the restriction endonuclease gene under control of the $P_{tac}$ promoter. The host strain used was *E. coli* which had been preprotected with the NlaIII methylase on a medium copy number plasmid pSYX20.

Previous reports by Bernan et al., ASM Abstracts 89: 206 (1989) and Brooks et al., J. Cell. Biochem. Supplemental 14A: 106 (1990) indicated that the restriction endonuclease gene might be contained on the methylase clone isolated from a partial PstI library even though there was no expression in the *E. coli* host. This had been the case with another restriction-modification system isolated from Streptomyces, SalI (Rodicio and Chater, Mol Gen Genet. 213: 349-353 (1988), Slatko et al. unpublished results). However upon DNA sequencing and amino terminal sequencing of the SphI restriction endonuclease, it was determined that the intact restriction endonuclease gene was not contained on the methylase clone.

Figure 1:
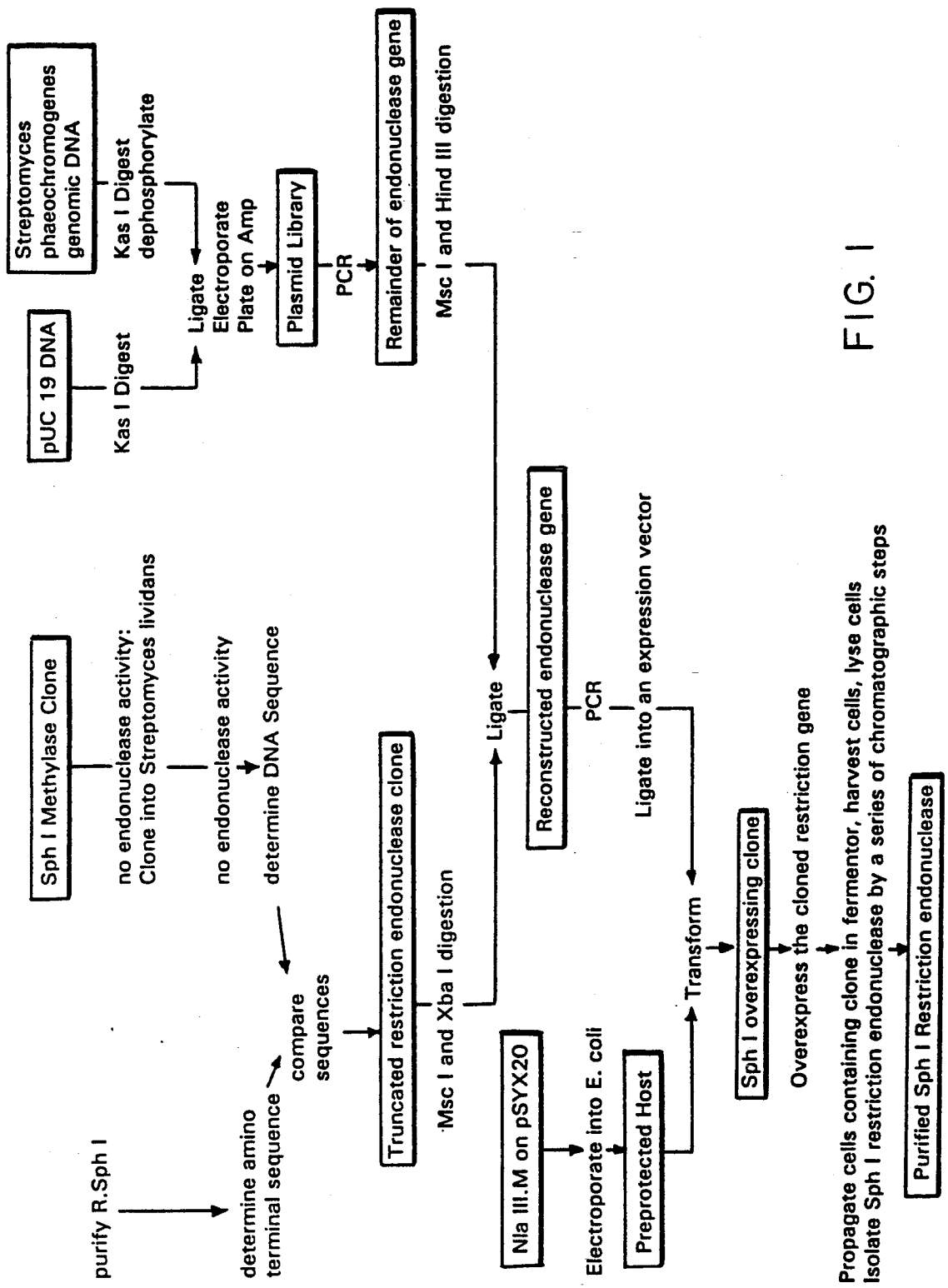
FIG. 1 illustrates the preferred method for cloning and producing the SphI restriction endonuclease. At the onset of the cloning project, it was not known which endonucleases or conditions would be successful in cloning the SphI restriction-modification system, nor where the restriction and modification genes were located within such clones. The cloning results and subsequent DNA sequencing, mapping, and characterization of the clones described in FIG. 1 and example 1 reveal the previously unknown direct pathway for cloning and expressing the SphI restriction-modification system.

The method described herein by which the SphI restriction gene is preferably cloned and expressed is illustrated in FIGS. 1 and includes the following steps:

1. The DNA of *Streptomyces phaeochromogenes* is purified.

2. The DNA is digested completely and/or partially with a restriction endonuclease such as PstI, or any of its isoschizomers, that cleaves the entire SphI methylase gene into a fragment(s). The fragment(s) should also be of cloneable size, that is, about 1.5-13 kb. It was found that other endonucleases that were tried did not satisfy the conditions described above these include ClaI, EcoRI, HindII, NdeI, NheI, NsiI, and XbaI.

3. pBR322 (or any other vector which has at least one SphI site preferably in an antibiotic resistance gene) is the prefered cloning vector since it contains one SphI site within the tetracycline resistance gene.

4. The digested DNA's are ligated to the cloning vector. The resulting mixtures are used to transform an appropriate host, i.e. a hsdR−, mcrBC− strain, such as *E. coli* strain RR1 or K802 (ATCC 31343 and ATCC 33526, respectively).

5. The DNA/cell mixtures are preferably plated on rich media containing an antibiotic, such as tetracycline, which is selective for transformed cells. After incubation, the transformed cell colonies are harvested together to form the primary cell libraries. As described above, a total of 10 such primary cell libraries were ultimately constructed using different combinations of cloning endonucleases and complete or partial digestion of the *Streptomyces phaeochromogenes* genomic DNA by the respective cloning endonuclease.

6. The recombinant plasmids are purified in toto from the primary cell libraries to make primary plasmid libraries.

7. The purified plasmid libraries are then digested to completion in vitro with the SphI restriction endonuclease which is prepared from *Streptomyces phaeochromogenes* cells, or any SphI isoschizomer such as BbvI or PaeI. SphI restriction endonuclease digestion causes the selective destruction of unmodified, non-methylase-containing clones, resulting in an increase in the relative frequency of SphI methylase-carrying clones. Exonuclease and/or phosphatase may also be added to the digestion to enhance the destruction of non-methylase clones.

8. Identification of SphI methylase clones: The digested plasmid library DNA's are transformed back into a convenient host such as *E. coli* strain RR1 or K802, and transformed colonies are again obtained by plating on antibiotic plates. The colonies are picked and their DNA is analyzed for the presence of the SphI modification gene in the following manner: The plasmid DNA is purified and incubated in vitro with SphI restriction endonuclease to determine whether it is resistant to digestion by SphI.

9. Once it has been established that the methylase gene has been cloned, the clone is assayed for SphI restriction endonuclease activity. If activity is detected, then the SphI restriction gene is linked to the methylase gene and is present in the clone. In such a case one could then skip to step 12 below. If no restriction activity is detected this indicates that the restriction gene is not linked to the methylase gene, or that it is linked but not cloned intact with the methylase gene, or that it is cloned intact but not expressed. In order to determine which of the above three possibilities is the true situation, the cloned fragment is restriction-mapped and deletions are made to determine where the relative position of the methylase gene is within the cloned fragment. The information is then used to determine if there is enough DNA on either side of the methylase gene to encode a restriction gene, if it were linked. If there is enough DNA, the restriction gene is assumed not to be linked, or to be present in the clone but not expressed (go to step 10). If there is not enough room on both sides of the methylase gene in the cloned DNA to encode a linked restriction gene, as was found for the PstI clone of the present invention, pSphM6.0, a portion of the methylase gene is used to probe digests of the *Streptomyces phaeochromogenes* chromosome to generate by Southern hybridization a genomic map of the region extending beyond the boundaries of the existing cloned DNA. This data helps identify certain endonucleases that cleave the restriction-modification region into individual fragments that carry the methylase gene as well as larger amounts of adjacent DNA. The exact sizes of the fragments generated by such endonucleases are calculated from the data as well. Presumably, if the restriction and modification genes are found to be linked, such fragments would also encode the restriction gene.

10. Past experience with restriction-modification systems isolated from Streptomyces or Nocardia has found that clones carrying the restriction endonuclease gene cannot be identified by the usual crude cell extract assay because of the low-level expression of the gene in *E. coli*. However, genes from Nocardia and Streptomyces can often be expressed to detectable levels when cloned in *Streptomyces lividans*. A fragment from the clone pSphM6.0 containing the methylase gene and possibly the endonuclease gene is subcloned onto a Streptomyces vector such as pIJ486 (described in the publication, Ward, J. M. et al., Mol. Gen. Genet. 203:468–478.) and transformed into *S. lividans*. The resulting clones in *S. lividans* are examined for methylase and endonuclease gene expression. If there is endonuclease expressed from the clone in *S. lividans*, then endonuclease gene is cloned but not expressed in *E. coli* (skip to step 12). If there is no expression as in the present invention the SphI endonuclease is purified as close to homogeneity as possible from *Streptomyces phaeochromogenes*, and the amino terminal sequence of the first 10 to 20 amino acids is determined. This protein sequence information is compared to the translated DNA sequence of the methylase clone to determine if the endonuclease gene is located on that cloned fragment, and if so, where the start of the endonuclease gene is located on that fragment. At the same time, the size of the restriction endonuclease protein is determined by protein gels to be approximately 27 kD. This indicates that the amount of DNA necessary to encode the endonuclease gene is approximately 0.8 kb. Clones carrying the SphI restriction endonuclease are identified as those that contain the sequence relating to the amino-terminus of the endonuclease and carry at least 0.8 kb of DNA downstream of that sequence. However, in accordance with the present invention, it was found that none of the methylase clones isolated contained enough DNA downstream of the endonuclease start to fully encode the endonuclease gene.

11. Cloning the remainder of the SphI restriction endonuclease gene: All attempts to clone the intact restriction endonuclease gene with or without the methylase gene into either *E. coli* or *S. lividans* host unprotected or preprotected with the SphI methylase failed. In order to obtain the SphI restriction endonuclease gene it is necessary to first clone only the 3' portion of the restriction endonuclease gene. A library of *S. phaeochromogenes* genomic DNA is constructed using a restriction endonuclease which cuts within and downstream of the 3' end of the restriction endonuclease gene as determined by Southern blot analysis. Once the library is prepared, the correct clone containing the 3' portion of the restriction endonuclease gene can either be identified by Grunstein colony or southern hybridization and then either isolated or amplified from the library using PCR amplification. With the clone of the fragment containing the 3' end of the restriction endonuclease gene isolated, the restriction endonuclease gene can be reconstructed to give the intact gene.

12. Overexpression: There are a number of ways in which the clone containing the restriction gene can be overexpressed. The DNA sequence, detailed mapping, and deletion data help determine the best approach for overexpression of the restriction endonuclease gene. One approach for overexpression comprises inserting a promoter recognized strongly by *E. coli*, such as $P_{tac}$ on pAGR3 (from W. Jack, New England Biolabs) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the $P_{tac}$ promoter. Alternatively, primers can be designed that hybridize directly in front of the restriction endonuclease gene and somewhere downstream of the restriction endonuclease gene in order to use the polymerase-chain reaction to amplify the entire restriction endonuclease gene. The resulting DNA fragment can be inserted into an expression vector such as pAGR3 directly downstream of an inducible promoter ($P_{tac}$). Other regulated promoters which can be used are PlacUV5 (Fuller, Gene 19:43–54, (1982)), and 1PL (Shimatake and Rosenberg, Nature 254:128, (1981)) on pUC19 and pBR322 derivatives, and a T7 promoter on the pET3A vector (from William Studier, Brookhaven National Lab., Upton, N.Y.). In addition, a strong ribosome binding site (Shine & Dalgarno, Proc. Natl. Acad. Sci. USA 71, 1342–1346, (1974)) can be placed in front of the gene to increase expression. In accordance with the present invention, to obtain a stable clone which overexpresses the restriction endonuclease, the host has to be preprotected from restriction endonuclease digestion. This is accomplished by cloning in either the SphI methylase, or a heterologous methylase such as NlaIII which protects from SphI digestion by modifying sites which overlap SphI restriction sites, on a separate plasmid. The plasmid used must be compatible with the expression vector. The methylase must also be produced at a level which will protect the host's genome from digestion by the overexpressed restriction endonuclease gene. In the present invention it was found that the SphI methylase gene cloned on a low copy number plasmid, such as pACYC184, did not give complete protection. By using the NlaIII methylase gene cloned on a medium copy number plasmid full protection of the host genome from SphI digestion was observed.

The DNA sequence of the gene can be altered by site-directed mutagenesis or by resynthesizing the gene itself to use codons that are more efficiently utilized in *E. coli* (Ikemura, J. Mol. Biol. 151:389–409, (1981)).

13. Production: The SphI methylase or endonuclease may be produced from clones carrying the SphI methylase gene (or a heterologous methylase) and the overexpressed restriction endonuclease gene by propagation in a fermenter in a rich medium with the appropriate antibiotic selection. The cells are thereafter harvested by centrifugation and disrupted by sonication to produce a crude cell extract containing SphI methylase and restriction endonuclease activity.

14. Purification: The crude cell extract containing the SphI methylase and endonuclease is purified by standard protein purification techniques such as affinity-chromatography, or ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be

EXAMPLE 1

Cloning of Sph I Modification Methylase and Restriction Endonuclease Genes

1. DNA purification: To prepare the DNA of *Streptomyces phaeochromogenes*, 1 g of cell paste was resuspended by shaking gently for 30 min in 5 ml of 0.1M Tris-HCl, 0.1M EDTA pH 7.6. The suspension was divided into two 3.0 ml portions. 3.5 ml of 1.7 mg/ml lysozyme in 0.1M Tris-HCl, 0.1M EDTA pH 7.6 was added to each portion and each was incubated for 15 minutes at 37° C. SDS was added to 1%, and proteinase K was added to 0.13 mg/ml and then the portions were incubated for 1 hour at 37° C. 0.4 ml of a solution of 10% SDS and 8% sarcosyl was added to each and incubation was continued at 55° C. for 2 hours. The two portions were then combined and dialyzed against four changes of DNA buffer (10 mM Tris-HCl, 1 mM EDTA pH 8.0) for 24 hours. The dialyzed DNA solution was then prepared for cesium chloride, ethidium bromide equilibrium density centrifugation by increasing the total volume to 40 ml with DNA buffer, and then dividing the DNA solution into two 20 ml portions, to each of which 20 grams of cesium chloride and 0.2 ml of 5 mg/ml ethidium bromide were added. The DNA solution was centrifuged at 44,000 rpm for 48 hours and the resulting band of DNA was removed with a syringe and an 18 gauge needle. The ethidium bromide was removed by extracting 4 times with an equal volume of ice-cold, water-saturated N-butanol. The cesium chloride was removed by dialysis. The DNA was then precipitated by adding NaCl to 0.5M and layering 0.55 volume isopropyl alcohol on top. The precipitated DNA was spooled onto a glass rod. The DNA was dissolved in 2 ml 10 mM Tris, 1 mM EDTA pH 8.0 to a final concentration of approximately 385 μg/ml.

NOTE FOR STEPS 2-10: As noted above, a total of 5 different restriction endonucleases were each used to digest the *S. phaeochromogenes* chromosome to construct and screen 10 libraries. Since only the partial PstI library yielded methylase clones, only the details for the partial PstI library will be provided. The other 9 libraries were prepared by methods similar to those outlined below.

2. Partial digestion: The purified DNA was cleaved with PstI to achieve partial digestion as follows: 100 ul of DNA at 500 ug/ml in 10 mM Tris pH 7.5, 10 mM MgCl$_2$, 100 mM NaCl, 10 mM β-mercaptoethanol buffer was divided into one 100 ul aliquot and seven, 50 ul aliquots. To the 100 ul tube was added 40 units of PstI to achieve 4 unit of enzyme per ug of DNA. 50 ul was withdrawn from the first tube and transferred to the second tube to achieve 2 units PstI/ug, and so on, each succeeding tube receiving half of the previous amount of PstI. The tubes were incubated at 37° C. for one hour, then heat-treated at 72° C. for 15 minutes and 15 ul from each was analyzed by agarose gel electrophoresis. Tubes exhibiting moderate, but incomplete digestion were chosen as the source of partial digest fragments for cloning. (The partial digestion tubes used were the 0.25 U/ug, 0.12 U/ug, 0.06 U/ug and 0.03 U/ug tubes) The separate reactions were mixed together and used as described in step 3 below.)

3. Ligation: The fragmented DNA was ligated to pBR322 as follows: 6 ug of PstI partially digested *Streptomyces phaeochromogenes* DNA (60 ul) was mixed with 3.0 μg of PstI-cleaved and dephosphorylated pBR322 (30 ul). 20 ul of 10X ligation mix (500 mM Tris pH 7.5, 100 mM MgCl$_2$, 100 mM DTT, 5 mM ATP) was added, plus 110.5 ul of sterile distilled water to bring the final volume to 198 ul. 7.5 ul of concentrated T4 DNA ligase ($2 \times 10^6$ U/ml) was added and the mixture was incubated at 17° C. for 4 hours then sterilized by the addition of 10 ul of chloroform. Approximately 62.5 ul of the ligated DNA was used to transform *E. coli* strain K802 as follows: The DNA was mixed with 0.5 ml of SSC/CaCl$_2$ (50 mM NaCl, 5 mM Na$_3$ Citrate, 67 mM CaCl$_2$) on ice and 1.0 ml of ice-cold competent *E. coli* K802 (hsdR$^-$M$^+$, mcrA$^-$, mcrBC$^-$ ATCC No. 33526) cells were added. After a 5 minute incubation at 42° C., the cells were diluted by the addition of 10 ml of Luria-broth (L-broth) then incubated at 37° C. for 4 hour.

4. Primary Cell Library: The transformed cell culture was briefly centrifuged, the supernatant was discarded and the cells were resuspended in 1.0 ml of L-broth. 200 ul portions were plated onto Luria-agar (L-agar) plates containing 25 ug/ml tetracycline. After overnight incubation at 37° C., the plates were each flooded with 2.5 ml of 10 mM Tris pH 7.5, 10 mM MgCl$_2$ and the transformed colonies were scraped together and pooled to form the primary cell library.

5. Primary Plasmid Library: The primary plasmid library was prepared as follows: 2.5 ml of the primary cell library was inoculated into 500 ml of L-broth containing 10 ug/ml tetracycline. The culture was shaken overnight at 37° C. then centrifuged at 4000 rpm for 5 minutes. The supernatant was discarded and the cell pellet was resuspended in 10 ml of 25% sucrose, 50 mM Tris pH 8.0, at room temperature. 5 ml of 0.25M EDTA pH 8.0, was added, followed by 3 ml of 10 mg/ml lysozyme in 0.25M Tris pH 8.0. The solution was left on ice for 3 hours, then 12 ml of lytic mix (1% Triton X-100, 50 mM Tris pH 8.0, 67 mM EDTA) was forcefully pipetted in, and the cell suspension gently swirled to achieve lysis. After lysis, the mixture was transferred to a 50 ml plastic centrifuge tube and spun at 17,000 rpm, 4° C. for 45 minutes. The supernatant was removed with a pipette. 20.0 g of solid CsCl was weighed into a 50 ml plastic screw-cap tube and 22.0 g of supernatant was pipetted into the tube and mixed. 1.0 ml of ethidium bromide solution (5 mg/ml ethidium bromide in 10 mM Tris pH 8.0, 1 mM EDTA, 100 mM NaCl) was added to the mixture. The solution was transferred to two 5/8 in. $\times$ 3 in. polyallomer centrifuge tubes and sealed. These tubes were then spun in a Beckman Ti70 rotor for 42 hours at 44000 rpm, and 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at $-20°$ C. to precipitate the DNA.

After precipitation, the solution was spun at 15000 rpm, 0° C. for 15 minutes and the supernatant discarded. The tube was left on the bench to air-dry for 15 minutes, then the DNA pellet was dissolved in 500 ul of DNA buffer and stored at −20° C. The DNA concentration of plasmids prepared in this way were found to be 100 to 200 ug/ml.

6. Digestion of Plasmid Pool: The gel-purified primary plasmid pool was digested to destroy non-SphI methylase clones as follows: The plasmid DNA was diluted to 30 ug/ml in SphI Buffer (50 mM NaCl, 10 mM Tris pH 8.0, 10 mM MgCl$_2$, 5 mM β-mercaptoethanol) A total of 900 ul was prepared. 16 U/ug SphI was added and the mixture was incubated at 37° C. for 2 hours. The enzyme in the reaction was killed by heating at 72° C. for 12 min. ExoIII nuclease was added to the digest at a concentration of 50 U/ug of DNA. After 1 hr of incubation at 37° C., 10 ul of chloroform was added to the tube. The chloroform was removed by centrifugation.

7. Transformation: A 12.5 ul sample from each tube was used to transform *E. coli* RR1. After the 3 minute incubation at 42° C. and 45 minutes of growth in L-broth at 37° C., the cell/DNA mixtures were plated onto L-agar plates containing 25 ug/ml tetracycline. After overnight incubation at 37° C., the plates were examined. Digestion of the plasmid library with SphI was found to have reduced the number of transformants by a factor of about $10^3$.

8. Analysis of surviving individuals: 28 of the surviving colonies obtained from section 7 were grown up into 10 ml cultures of L-broth containing tetracycline and the plasmids that they carried were prepared by the following miniprep plasmid purification procedure, adapted from the method of Birnboim and Doly (Nucleic Acids Res. 7: 1513 (1979)).

Miniprep Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells and then placed on ice. Once the solutions had cleared, 1.5 ml of 3M sodium acetate pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 ul of 10 mM Tris, 1 mM EDTA pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris pH 8.0, 1 mM EDTA, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded, and the pellets were redissolved in a final solution of 150 ul of 10 mM Tris, 1 mM EDTA pH 8.0.

The plasmid minipreps were subsequently analyzed by digestion with SphI.

Figure 2:
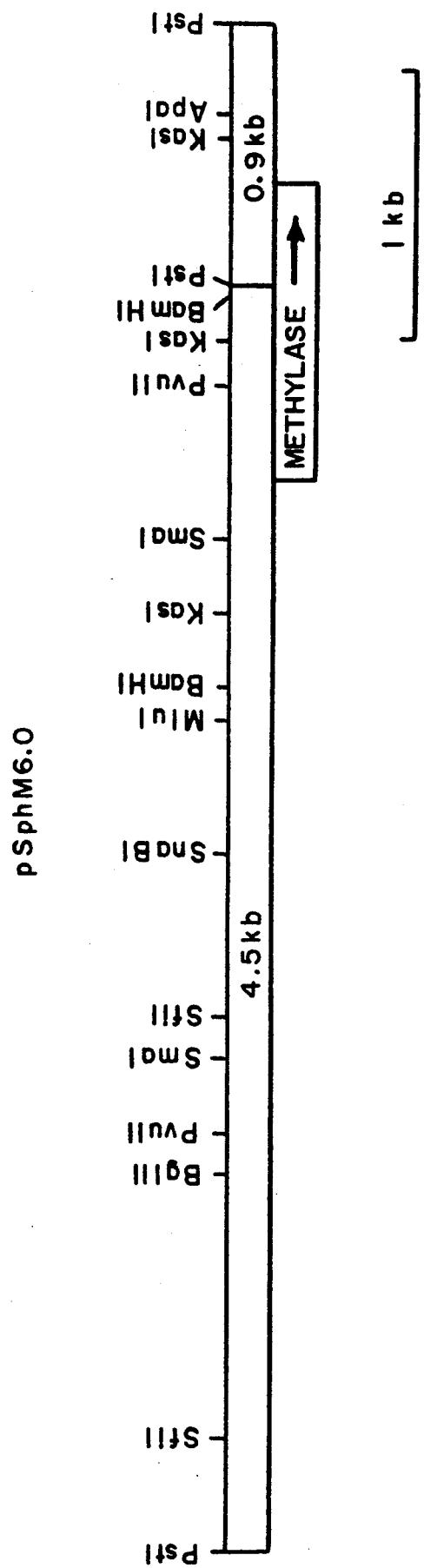
FIG. 2 is a map of the PstI partial clone pSphM6.0 obtained from the methylase selection of the PstI library.

9. Methylase Gene Clones: One plasmid was found to be resistant to SphI and to carry two PstI fragments (FIG. 2). An in vitro restriction assay was performed on the extract prepared from the *E. coli* clone, as follows:

A 50 ml culture of the clone to be tested for endonuclease activity was grown overnight in L-broth plus 25 ug/ml tetracycline at 37° C. The cells were pelleted by centrifugation at 5000 rpm for 5 minutes. The supernatant was discarded and the pellet was resuspended in 3 ml of sonication buffer (20 mM KPO$_4$ pH 7.4, 10 mM β-mercaptoethanol). Lysozyme was added to the cell suspension to a final concentration of 200 ug/ml. This mixture was kept on ice for 3 hr, then frozen at −20° C. The mixture was thawed on ice and 2 ml of this suspension was mixed with 2 ml sonication buffer. 0.4 ul of a 25% solution of Triton X-100 was added to the suspension and mixed by pipetting up and down. The disrupted cells were spun for 10 minutes at 5,000 rpm. The supernatant was assayed for restriction endonuclease activity by incubating 7.5 ul of the cell extract with 120 ul of 1X SphI Buffer, and 50 ug/ml pBR322 DNA (predigested with PstI) for 2 hr. at 37° C. A 15 ul sample checked by electrophoresis showed no evidence of restriction endonuclease activity.

10. Location of the methylase gene within the 4.5 and 0.9 kb PstI inserts: The SphI methylase clone was digested with numerous restriction endonucleases to provide a restriction map of the cloned DNA. Using the map, various regions within the insert were deleted to determine the resulting affect upon methylation. The location of the ∼1 kb methylase gene spanning the PstI site was then pinpointed, and the length of cloned DNA on either side of the gene was found to be 3.5 and 0.4 kb. The methylase clone would not have enough DNA (0.4 kb) on the right side of the methylase gene to encode a linked restriction endonuclease gene, but would have enough room on the left side of the methylase gene. However, since the distance between the two genes, the exact size of the genes, and whether or not they were linked was not known, the lack of SphI endonuclease activity in the clone indicated that the restriction gene was either not present in the clone, or was present but not expressed. In the event that the restriction gene was present and not expressing, the cloned methylase gene with adjacent DNA was subcloned into a Streptomyces vector which was used to transform *Streptomyces lividans* (step 11, 12). In addition, DNA sequencing and protein sequencing of the methylase clones were undertaken to determine whether part, all or none of the restriction gene was present in the clones steps 13–14). In the event that the entire restriction gene was not present, the cloning of larger regions of DNA adjacent to the methylase gene was achieved (steps 15–17).

11. Cloning the SphI methylase subclones into *S. lividans:* With the methylase clone, there was enough DNA cloned on one side of the methylase gene to encode a restriction endonuclease gene, if it were linked, and depending on the exact location of the methylase gene. However, since the clone did not express any restriction endonuclease activity, and with still no proof that the two SphI restriction-modification genes were linked, it was decided to try to clone the methylase subclones into *S. lividans*, a species more closely related to *S. phaeochromogenes* than *E. coli* [Below is described the cloning of the 3.6 kb ApaI-BglII fragment from pSphM3.6; a similar subcloning experiment was performed with a 2.6 kb ApaI-SnaBI fragment isolated from pSphM2.6 (see FIG. 2 for location of sites). The results were the same, so for brevity, only the ApaI-BglII subcloning will be described in detail here.] 15 ul (1.0 ug) of pSphM3.6 was digested in 50 ul of 10 mM Tris pH 7.5, 10 mM $MgCl_2$, 100 ug/ml bovine serum albumin, 50 mM NaCl containing 20 U of EcoRI 20 U of ScaI and 20 U of HindIII at 37° C. for 2 hr. The entire volume was electrophoresed in a 0.7% agarose gel for 2 hr. The 3.6 kb EcoRI-HindIII restriction fragment was collected by electrophoresing into DEAE anion exchange paper for 2 hr. The paper was washed two times in 150 ul of a buffer containing 0.1M NaCl, 10 mM Tris pH 8.0, and 1 mM EDTA. Subsequently, the DNA was eluted from the paper by washing the paper four times with 75 ul of a buffer containing 1.0M NaCl, 10 mM Tris pH 8.0 and 1 mM EDTA. The resulting solution containing the DNA fragment was extracted with 300 ul phenol/chloroform followed by extraction with 300 ul chloroform and precipitated with 1 ml absolute ethanol by placing in a dry ice/ethanol bath for 15 min. The DNA was pelleted at 14,000 rpm for 5 min. The pellet was rinsed with 70% ethanol, air dried and resuspended in a final volume of 10 ul 10 mM Tris pH 8, and 1 mM EDTA. 10 ul (0.5 ug) of the EcoRI-HindIII purified DNA fragment was ligated to 2 ul (0.2 ug) of EcoRI-HindIII cleaved and dephosphorylated pIJ486 (pIJ486 was obtained from Hopwood, D.A. of Norwich, England) in a final volume of 50 ul in 1×ligation buffer containing 1 ul T4 DNA ligase (400 U) at 12° C. overnight. 10 ul of the ligation mix was added to approximately $4 \times 10^9$ S. lividans TK24 (obtained from Hopwood, D. A. TK24 is described in Hopwood, D. A., et al., *Genetic Manipulation of Streptomyces, a Laboratory Manual*) protoplasts, prepared as described in Hopwood D. A., et al., ibid, in P Buffer [103 g Sucrose, 0.25 g $K_2SO_4$, 2.02 g $MgCl_2.6H_2O$, 2 ml Trace elements solution, and distilled water to 800 ml. 80 ml aliquots are dispensed and autoclaved. Before using the following is added to each 80 ml: 1 ml 0.5% $KH_2PO_4$, 10 ml 3.68% $CaCl_2.2H_2O$ and 10 ml 5.73% TES buffer pH 7.2. Trace elements solution per liter: 40 mg $ZnCl_2$, 200 mg $FeCl_3.6H_2O$, 10 mg $CuCl_2.4H_2O$, 10 mg $MnCl_2.4H_2O$, 10 mg $Na_2B_4O_7.10H_2O$ and 10 mg $(NH_4)_6Mo_7O_{24}.4H_2O$] 0.5 ml of 25% polyethylene glycol 1000 was added to the protoplast/DNA mixture. This was drawn up and down 3 times in a 1 ml pipette. 0.1 ml of the transformation mix was plated on each of six R2YE plates [103 g Sucrose, 0.25 g $K_2SO_4$, 10.12 g $MgCl_2.6H_2O$, 10 g glucose, 0.1 g Difco casamino acids and 800 ml $H_2O$. 80 ml of this solution is mixed with 2.2 g Difco agar and autoclaved. To prepare the plates the base agar solution is melted and the following sterile solutions are added: 1 ml 0.5% $KH_2PO_4$, 8 ml 3.68% $CaCl_2.2H_2O$, 1.5 ml 20% L-proline, 10 ml 5.73% TES buffer pH 7.2, 0.2 ml Trace elements solution, and 0.5 ml 1N NaOH. The plates are poured and dried in a laminar flow hood for at least one hr.]. The plates were overlayed after incubating overnight at 30° C. with 1.0 ml of an aqueous solution of thiostrepton (0.5 mg/ml). The plates were returned to 30° C. for 3 to 4 days until the colonies have grown.

12. Analysis of transformants: the colonies obtained from the thiostrepton selection were streaked on R2YE plates containing 5 ug/ml thiostrepton for isolated colonies. Once grown, these were used to inoculate 5 ml of TSB, Oxoid Tryptone Soya Broth, with 5 ug/ml thiostrepton. These cultures were incubated at 30° C. with aeration for 24 hr. Minipreps were done on 1 ml of the cultures. This procedure is identical to the procedure described by Birnboim and Doly (Nucleic Acids Res. 7:1513 (1979)) with the exception that a 30 minute incubation in 4 mg/ml of lysozyme, 50 mM glucose, 25 mM Tris pH 8.0, and 10 mM EDTA at 37° C. is necessary before adding the NaOH-SDS solution. 10 ul of the miniprep DNA was analyzed by running on an 0.7% agarose gel. 2 of the 6 clones appeared to have the correct sized fragment inserted in pIJ486. Spores from these two isolates were harvested and used to inoculate 500 ml TSB with 5 ug/ml Thiostrepton. CsCl plasmid preps were prepared on the cultures following a scaled up (20X) version of procedure 3, p.93 in Hopwood et al. ibid. The resulting pellet was resuspended in 17 ml 10 mM Tris pH 8.0, 1 mM EDTA, 18.7 g CsCl and 0.44 ml ethidium bromide (5 mg/ml). The solution was transferred to two ⅝ in.×3 in. polyallomer centrifuge tubes and sealed. These tubes were centrifuged in a Beckman Ti70 rotor for 44,000 rpm for 48 hr, 17° C. To collect the plasmids, the tops of the tubes were pierced with a scalpel and the lower of the two fluorescent DNA bands was collected by syringe under ultraviolet light. The lower band from both tubes was combined into a 15 ml Corex tube and the ethidium bromide was removed by adding an equal volume of water and three volumes of ethanol. After 2 hr at −20° C. the DNA was pelleted by spinning at 12,000 rpm for 20 min. The pellet was resuspended in 2 ml 10 mM Tris pH 8.0, 1 mM EDTA. 50 ul of 8M LiCl was added and the DNA was extracted with phenol/chloroform followed by a chloroform extraction. The DNA was precipitated by adding 3 volumes ethanol to the aqueous solution as described above. The pellet was resuspended in 500 ul 10 mM Tris pH 8.0, 1 mM EDTA. The purified plasmid was digested with EcoRI and HindIII to confirm the presence of the insert as well as with SphI to determine if the subclone in S. lividans had any SphI methylase activity. Both subclones were apparently identical having the correct construction as well as having methylase activity i.e., were unable to be digested with the SphI restriction endonuclease. To test for SphI restriction endonuclease activity 50 ml of culture grown identically to that used for the plasmid prep was pelleted. The pellet was washed with 10.3% sucrose and frozen at −70° C. Upon thawing the pellet was resuspended in 3 ml/g of wet cell weight with a solution of 50 mM Tris pH 8.0, 7 mM β-mercaptoethanol, 1 mM PMSF 1 mM Na Azide, and 200 mM NaCl. After sonication on ice the debris were removed by centrifugation at 16,000 rpm for 45 min. The supernatant was assayed for SphI restriction endonuclease activity. These subclones, denoted pEGsphM2-4, and pEGsphM2-6, had no detectable SphI endonuclease activity in S. lividans. Indicating that either the SphI restriction endonuclease gene was not linked to the SphI methylase gene or that the restriction endonuclease gene was not intact on the SphI methylase clone.

13. To try to determine if the endonuclease gene was present on the cloned fragments, and if so, where, the SphI restriction endonuclease was purified as close to homogeneity as possible as follows:

1.1 liters of crude cell extract from 413 g of *Streptomyces phaeochromogenes* was placed over the following columns in the following order: Phosphocellulose, Heparin-Sepharose, Q-Sepharose, MonoQ HPLC, and Mono-S HPLC resulting in ~50% pure SphI restriction endonuclease preparation.

25 to 30 pM of the purified SphI restriction endonuclease was used for amino terminal protein sequencing on Applied Biosystems Model 470A gas phase protein sequencer. The first 13 amino acid residues of the restriction endonuclease were determined to be: Thr Ser Lys Asp Pro Ile Val Leu Ser Ala Asp Gln Ile (SEQ ID NO:1)

14. DNA sequencing of the region confirmed that 5' region of the restriction endonuclease gene was present on the partial PstI clone pSphM6.0 but that the entire restriction endonuclease gene was not present on the clone, that the restriction gene was downstream of the methylase gene, and that it was being transcribed in the same direction as the methylase gene (SEQ ID NO:2). The sequence also provided data to use as a basis for subsequent manipulations to clone the remainder of the restriction endonuclease gene and then to induce expression of the cloned gene in *E. coli*.

15. A genomic map of the adjacent regions was determined using the Southern blot technique (Southern, E. 1975, J.Mol.Bio., 98:503) to determine what enzymes would be most useful for cloning the remainder of the restriction endonuclease gene. Several clones containing either a portion or all of the methylase gene were used to probe the southerns, specifically, the 0.9 kb PstI fragment or the 1.4 kb SmaI-ApaI fragment (FIG. 2) cloned in pUC19. These plasmids were nick-translated as follows: 1 ul (0.5 ug) DNA, 10 ul buffer (500 mM Tris pH 7.8, 100 mM β-mercaptoethanol, 50 mM MgCl$_2$), 4 ul dNTP's (0.1 mmole each), 5 μl alpha-$^{32}$P-dCTP (100 pmoles, 800 Curies/millimole), 1 ul DNA polymerase I (20 units), 1 ul DNAse I (1 ug/ml) and 78 ul of H$_2$O were mixed together and incubated 15° C. for 3 hr. The mixture was then boiled for 5 minutes and placed immediately on ice.

The Southern blot was prepared as follows: *S. phaeochromogenes* DNA was digested separately with the restriction endonucleases ApaI, BamHI, BclI, BglII, BstYI, EcoRI, KasI, MluI, MscI, PvuII, PmlI, SacI, SalI, SacII, SfiI, SmaI, SnaBI, and StuI. The digests were electrophoresed on a 1.0% agarose gel. The gel was soaked in 0.25M HCl for 10 min; twice in 0.5M NaOH, 1.5M NaCl for 30 min each; and then twice in 0.5M Tris pH 7.5, 1.5M NaCl for 30 min each. A nitrocellulose sheet was soaked briefly in water, then in 10×SSC (1.5M NaCl, 150 mM Na$_3$Citrate). A sandwich was constructed of a 2 inch stack of paper towels, 2 sheets of Whatman 3MM paper (soaked in 10 ×SSC) one sheet of the wetted nitrocellulose membrane, the treated agarose gel, another sheet of nitrocellulose membrane, two more sheets of 3MM paper and 2 inches of paper towels. The sandwich was weighted down and transfer of the DNA to the nitrocellulose sheets was allowed to proceed at room temperature overnight. The nitrocellulose sheets were then rinsed in 0.9M NaCl, 90 mM Na$_3$Citrate for ten minutes and baked in a vacuum oven at 80° C. for 1.5 hr. to fix the transferred DNA fragments to the nitrocellulose. The sheet was placed in a plastic bag containing 15 ml of a solution composed of 4 ml of 20 g/l Ficoll, 20 g/l polyvinylpyrrolidone, 20 g/l bovine serum albumin; 15 ml of 20×SSC (4.5 ml of 3M NaCl, 0.3M Na$_3$Citrate); 1 ml of 100 mg/ml denatured and sonicated salmon sperm DNA; and 80 ml H$_2$O. The sheet was prehybridized by incubating at 65° C. shaking for 2 hr. 100 ul of the radioactive probe was added to the bag, and incubation was continued at 65° C. shaking overnight. The nitrocellulose sheet was then washed two times for 30 minutes each at 65° C. with 2×SSC and 0.1% SDS and 30 minutes at 65° C. in 0.2×SSC and 0.1% SDS. The sheet was then air-dried and autoradiographed overnight.

From the Southern blot data, the approximate sizes of 10 endonuclease encoding fragments were known. ApaI, BamHI, BstYI, KasI, MluI, PvuII, SacI, SmaI and StuI fragments carry DNA to the right of the methylase gene; (FIG. 2). The probe hybridized to a 1.2 kb band in the ApaI digest, a 7.5 kb band in the BamHI digest, a 4.9 kb band in the BstYI digest, a 0.9 kb band in the KasI digest, a 3.6 kb band in the MluI digest, a 1.8 kb band in the PvuII digest, a 4.5 kb band in the SacI digest, a 2.4 kb band in the SmaI digest and a 7.5 kb band in the StuI digest. The other bands were judged to be too large to clone.

Figure 3:
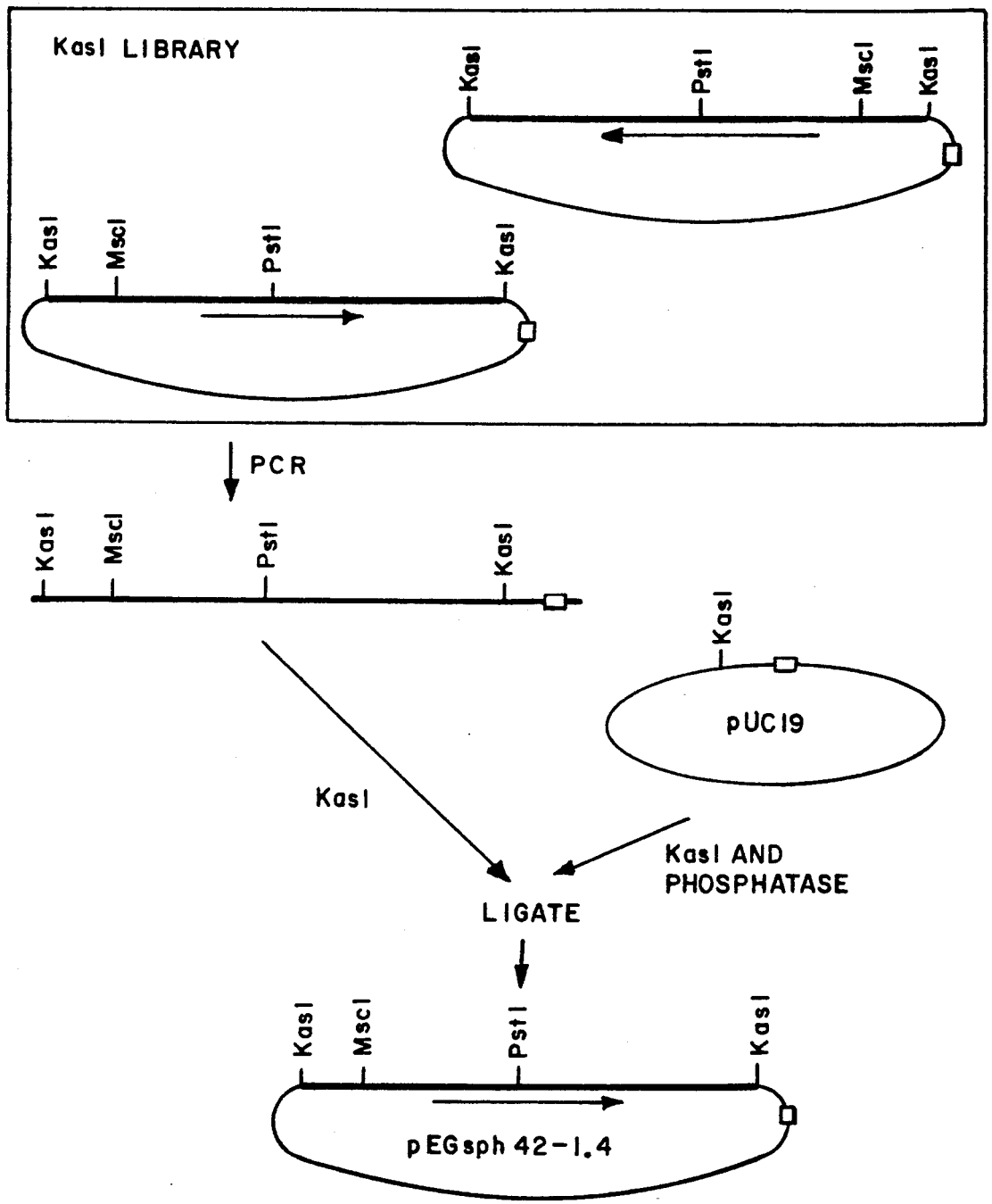
FIG. 3 is a schematic diagram of the isolation of the remainder of the SphI restriction endonuclease gene from a KasI library prepared from *S. phaeochromogenes* genomic DNA. The large stippled box at the top of the figure represents the KasI library. The two circles represented with in the box are the two plasmids, among many different clones, which contain the remainder of the SphI restriction endonuclease gene (as indicated by the long arrow with in the circle). The arrow heads indicate where the primers used to amplify the desired fragment out of the KasI library would anneal The small box on the plasmids indicates the location of the multiple cloning site on the vector.

16. Isolation of a clone carrying the region downstream of the SphI methylase gene: Since all attempts to clone the intact SphI restriction endonuclease gene with or with out the methylase into either an *E. coli* or *S. lividans* host which were unprotected or preprotected with the SphI methylase were unsuccessful, an attempt was made to clone only the 3' end of the restriction endonuclease gene. From the DNA sequence and Southern analysis it was determined that KasI (or NarI) cuts within the restriction endonuclease gene and that the next site, approximately 0.9 kb downstream, should cleave the DNA downstream of the 3' end of the restriction endonuclease gene. Cloning the 0.9 kb KasI fragment should give the remainder of the restriction endonuclease gene. A KasI library was made of *S. phaeochromogenes* genomic DNA by taking 100 ul (9 ug) of genomic DNA and digesting in 120 ul of 10 mM Tris-HCl, 10 mM MgCl$_2$, 50 mM NaCl, 1 mM DTT pH 7.9, 100 ug/ml BSA, and 20 U KasI at 37° C. for 2 hr. The entire volume was electrophoresed in a 0.7% agarose gel for 2 hr. DNA fragments ranging in size from 0.7 to 1.0 kb were collected by electrophoresing into DEAE anion exchange paper for 2 hr. The DNA was eluted from the DEAE paper as described in step 11. The pelleted DNA was resuspended in 20 ul 10 mM Tris pH 8.0 and 1 mM EDTA. 20 ul (~0.5 ug) of the purified KasI digested fragments were ligated to 5 ul (0.2 ug) of KasI cleaved and dephosphorylated pUC19 in a final volume of 50 ul in 1×ligation buffer containing 1 ul T4 DNA ligase (400 U) at 4° C. for 48 hr. 10 ul of the ligation was deionized by drop dialysis using a Millipore VS 0.025 uM filter. The DNA was then electroporated into *E. coli* ED8767. The *E. coli* was prepared for electroporation by growing up 1 l of cells to Klett 50–80 in L-broth. The cells were chilled on ice for 15 to 30 min and then pelleted in the cold at 4,000 rpm for 15 min. The pellet was washed 2 times in ice cold sterile water and once in 10% glycerol. The washed pellet was resuspended in 1 to 2 ml of 10% glycerol to a final cell concentration of 3×10$^{10}$ cells per ml. The cells were frozen until needed in 100 ul aliquots at −70° C. To electroporate the DNA into the prepared cells, the cells were gently thawed and placed on ice. 40 ul of cells were mixed with 10 ul of the ligated and dialyzed DNA. The mixture was placed into a cold 0.2 cm electroporation cuvette. A pulse of electricity at 12.5 kV/cm with a time constant of 4–5 msec was applied to the DNA cell mixture. The *E. coli* was immediately diluted with 2 ml L-broth, allowed to grow at 37° C. for 1 hr and then plated on 8 150 mm L-agar with ampicillin. After overnight incubation at 37° C., the plates were flooded with 10 ml L-broth and the colonies were scraped together. Each plate was pooled separately to form sub-libraries containing between 5,000 to 6,000 colonies each. 0.2 ml of glycerol was added to 0.8 ml of each sub-library and kept at −70° C. as a frozen stock. Plasmids were isolated from the cells in the remaining 9 ml of each sub-library using the miniprep procedure as described by D. Ish-Horowicz (In: *Molecular Cloning, a Laboratory Manual* by T. Maniatis, E. F. Fritsch and J. Sambrook, Cold Spring Harbor Laboratory Press, 1982, pp 368–369.) except that the entire procedure was scaled up 5 fold. The final DNA pellet was resuspended in 8.5 ml 10 mM Tris pH 8.0, 1 mM EDTA, 9.35 g CsCl and 0.25 ml ethidium bromide (5 mg/ml). The gradients were formed and the DNA was purified as described in step 12. Once purified the plasmids from the sub-libraries were digested with KasI, run on an agarose gel, blotted and probed with pSph0.9 as described in step 15. 3 of the 8 sub-libraries had the desired 0.9 kb KasI fragment which hybridized to the 0.9 kb PstI fragment used as the probe. To amplify this fragment from these sub-libraries, two oligonucleotide primers were prepared. Primer 1 contains a portion of the pUC19 sequence 5′ of the KasI site and a region of the restriction endonuclease gene which had been cloned and sequenced 3′ of the KasI site: 5′ CGC ATC AGG CGC CGT CAC CAC GGG C 3′, SEQ ID NO:3. Primer 2 is the M13/pUC reverse sequencing primer produced by New England Biolabs product #1233. The 3′ segment of the SphI restriction endonuclease gene with a portion of the cloning vector pUC19 was amplified from the sub-libraries by a PCR reaction with 1 U Vent® DNA polymerase in 10 mM KCl, 10 mM (NH4)2SO4, 20 mM Tris-HCl (pH 8.8), 2 mM MgSO4, 0.1% Triton X-100, 200 uM each dNTP, 100 ug/ml BSA, 5% DMSO at 95° C. for 1.5 min, 60° C. for 1.5 min and 72° C. for 2 min, for 20 cycles. The reactions were electrophoresed in a 0.7% agarose gel. Fragments approximately 1.0 to 1.2 kb in size were purified using DEAE paper as described in step 11. The purified fragments were digested with KasI and ligated into KasI digested dephosphoralated pUC19. The ligation was electroporated into *E. coli* ED8767 and plated on L-agar with ampicillin. Plasmid DNA minipreps were prepared on 36 isolated colonies using the procedure described by Ish-Horowicz (In: Maniatis et al. Ibid). One of the 36 colonies contained a plasmid which had the correct sized insert of 0.9 kb. Restriction mapping indicated that it contained the correct restriction enzyme sites. Southern analysis showed that the newly isolated clone hybridized to pSph0.9, indicating that the fragment cloned was probably the desired fragment. Since the 0.9 kb KasI fragment contained only the 3′ portion of the SphI restriction endonuclease gene it was impossible to test for endonuclease activity until the gene had been reconstructed. The clone was named pEGsph42-1.4 (FIG. 3).

Figure 4:
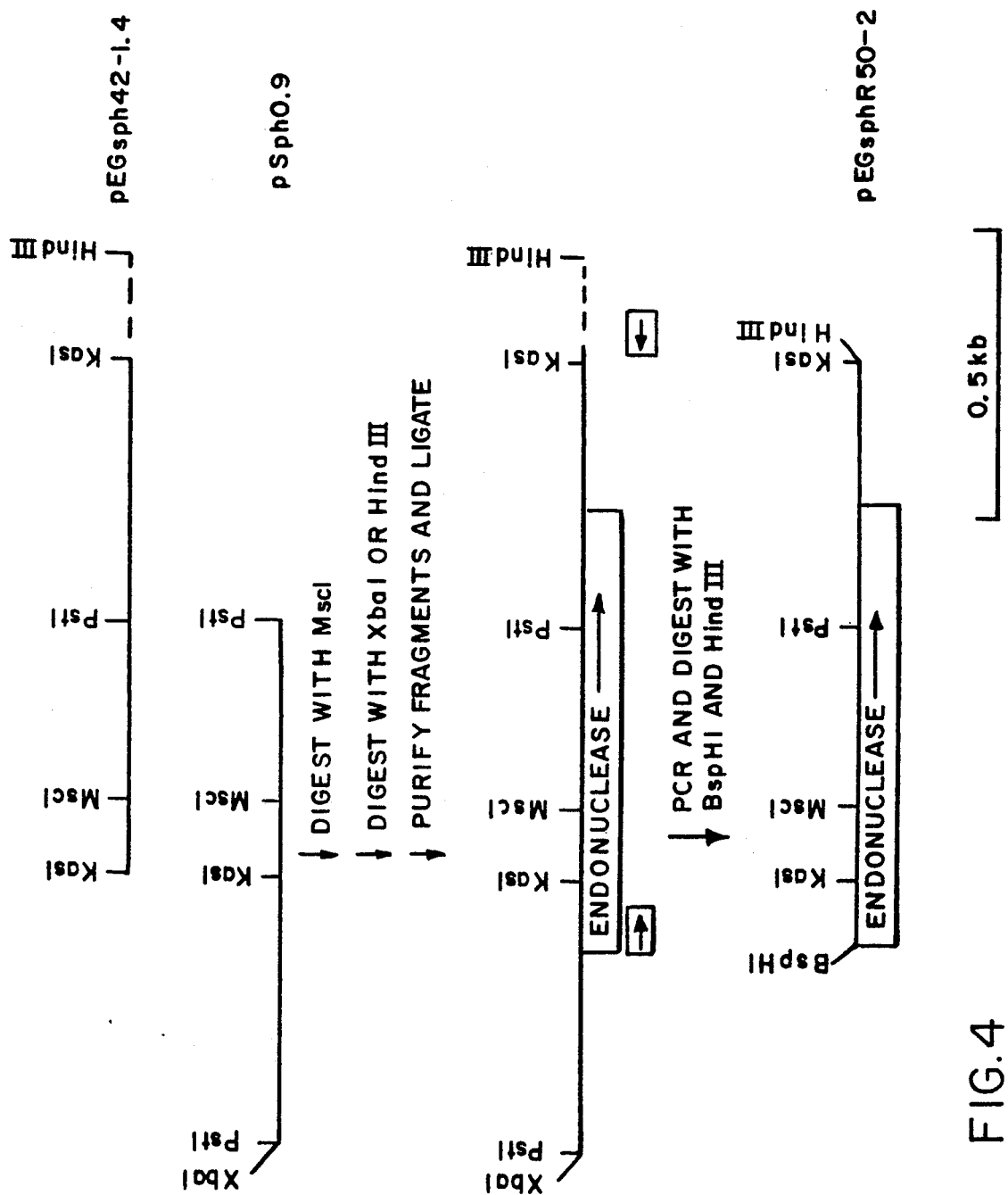
FIG. 4 is a schematic diagram of pEGsph42-1.4 and the reconstruction of the restriction endonuclease gene and PCR to give pEGsphR50-2. pSphM0.9 is the 0.9 kb PstI fragment from pSphM6.0 cloned into pUC19. The XbaI site indicated on the map of pSphM0.9 is a site within the vector and is not part of the DNA which encodes the SphI restriction modification system. The dashed line in pEGsph42-1.4 indicates that this region on the map is from the vector pUC19 (including the HindIII site noted). The heavily boxed arrows drawn below the reconstructed endonuclease gene indicate the location and direction of the primers used to PCR the endonuclease gene to construct pEGsphR50-1 for overexpression.
Figure 5:
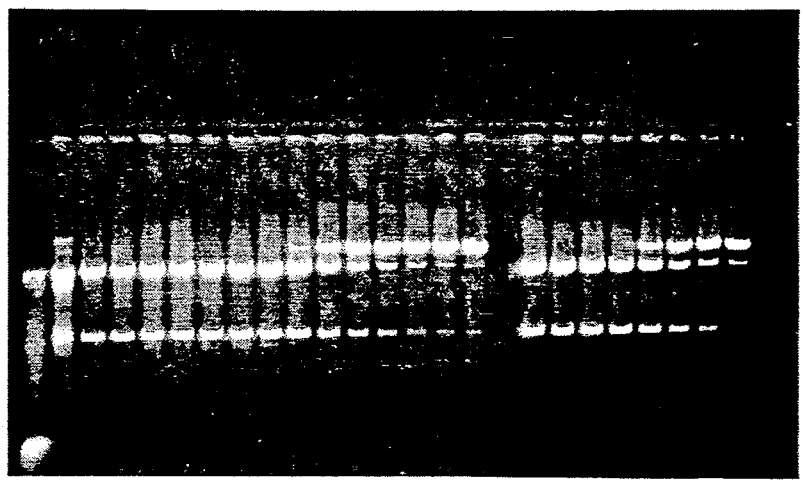
FIG. 5 is a photograph of an agarose gel illustrating the titer of SphI restriction endonuclease activity obtained from the cell extracts of NEB# 808. The numbering of the lanes on the gel is from left to right with lane 1 on the left side of the gel and lane 25 on the right. A DNA mixture was made by taking 16 ul of pBR322 (16 ug) 80 ul of 10X NEBuffer 2, 10 ul PstI (200 U) and bringing up to 800 ul with sterile water. 1 ul of the crude extract prepared from NEB# 808 was added to 49 ul of the DNA mixture (FIG. 5, lane 1). After mixing 5 ul was removed from this tube and added to a second tube with 45 ul of the DNA mixture (FIG. 5, lane 2). 5 ul was removed from the second tube and added to a third tube with 45 ul of the DNA mixture (FIG. 5, lane 3). 25 ul is removed from the third tube and added to a fourth tube with 25 ul of the DNA mixture (FIG. 5, lane 4). 6 further 1:1 dilutions are performed (FIG. 5, lanes 5 to 16). Similar 1:1 dilutions are done on 1 ul of SphI purified from *S. phaeochromogenes* (FIG. 5, lanes 18 to 25) to estimate the titer of the enzyme in the crude extract. After incubation at 37° C. for 1 hr, 25 ul from each dilution are loaded on a 0.7% agarose gel which is run for 2 hr.

17. Reconstruction and overexpression of SphI restriction endonuclease: The restriction endonuclease gene was reconstructed by taking 10 ul (5 ug) of pEGsph42-1.4 and 3 ul (5 ug) of pSph0.9 were separately digested with MscI in 1×NEBuffer 4 (20 mM Tris-acetate, 10 mM magnesium acetete, 50 mM potassium acetate, 1 mM DTT pH 7.9 for 2 hr at 37° C. After incubation the digests were extracted once with a 1:1 mixture of phenol:chloroform, once with chloroform, and precipitated with 1/10 volume of 3M sodium acetate and 2.5 volumes of 95% ethanol. The DNA were pelleted by centrifugation in an Eppendorff centrifuge for 5 min at room temperature and washed once in 70% ethanol. The pellets were resuspended in 1×NEBuffer 2. The MscI digested pSph0.9 was further digested with the addition of 20 U of XbaI and the MscI digested pEGsph42-1.4 was further digested with the addition of 20 U HindIII. After 2 hr at 37° C. the DNA was run on a 0.7% agarose gel. A 0.6 kb band was purified from the digest of pSph0.9 and a 1 kb band was purified from the digest of pEGsph42-1.4 using the Bio-Rad Prep-A-Gene kit as per manufactures instructions. The two fragments (∼0.5 ug of each) were ligated in 1X Ligase Buffer and T4 DNA Ligase (400 U) at 12° C. for 18 hr (FIG. 4). Since all attempts to clone this ligated fragment into a high copy plasmid in an *S. lividans* host preprotected with the SphI methylase failed, it was decided to try to directly clone the reconstructed fragment behind a regulated *E. coli* promoter. Two oligonucleotide primers were made using the DNA and protein sequence data. The first oligonucleotide primer contained the sequence which overlaps the AUG codon, indicated by protein sequencing to be the start of the endonuclease gene, with two bases changed to create a BspHI site: 5′ CCT TCG ACT ATA GTG AAG TCA TGA CAA G 3′ SEQ ID NO:4. The second oligonucleotide primer contains sequence to the left of the KasI site in pUC19 with a HindIII site included in the primer to aid the cloning of the fragment once amplified: 5′ GCG CAG CCT GAA TGA AGC TTG GCG CC 3′ SEQ ID NO:5. These two primers were used with the ligated fragments from pSph0.9 and pEGsph42-1.4 (described above) as the template in PCR (using the conditions described in step 16) to amplify a 1 kb DNA fragment. The band was purified using DEAE paper as described in Step 11. Once purified the PCR product was digested with 2 U of BspHI in 1×NEBuffer 4 for 2 hr and then with 20 U HindIII in 1×NEBuffer 2 and purified from an agarose gel using DEAE paper (FIG. 4). The purified fragment (∼0.1 ug) was ligated into the $P_{tac}$ expression vector, pAGR3 (from W. Jack, New England Biolabs) which had been digested with NcoI and HindIII (∼0.05 ug) in a total volume of 40 ul with 400 U of T4 DNA ligase at 37° C. for 2 hours. (pAGR3 is a pBR322 based vector which contains an ampicillin resistance gene, a single copy of lacI$^q$, the $P_{tac}$ promoter, a 4 fold direct repeat of rrn$_b$ terminator upstream of the $P_{tac}$ promoter to prevent read-through transcription, and an NcoI site downstream of a lac ribosome binding site.) 20 ul of the ligation was used to transform competent *E. coli* ED8767 which carried the NlaIII methylase gene on pSYX20. [The NlaIII methylation recognition site, CATG, overlaps the SphI restriction endonuclease recognition site and so protects the host from SphI digestion. pSYX20 (ATCC# 75260) is a medium copy number plasmid that carries Kan$^r$ and Tc$^r$ genes on a pSC101 replication origin. A methylase gene inserted into the Tc$^r$ gene can be expressed constitutively from the Tc promoter.] The transformed cells were grown for 30 min. at 37° C. and plated on L-agar with ampicillin (100 ug/ml) and kanamycin (50 ug/ml). 36 colonies were picked and streaked onto L-agar with ampicillin and kanamycin for isolated colonies. Plasmids were isolated from the individual colonies using mini plasmid prep procedure as described in step 8. HindIII digests of 5 ul of each miniprep were compared with HindIII digests of pAGR3. 24 of the 36 clones appeared to have a plasmid which was larger than pAGR3. Six of these clones were chosen for further characterization. These 6 clones were grown in 200 ml L-broth with ampicillin and kanamycin to a Klett of 60 (mid log phase) and induced with 1 mM IPTG. 50 ml of culture was removed at 2 hours after induction. The cells were harvested by centrifugation, washed once in cold Sonication buffer (50 mM NaCl, 1 mM PMSF and 1 mM $\beta$-mercaptoethanol, 50 mM NaCl, 1 mM PMSF and 1 mM sodium azide) and the pellet was frozen at $-70°$ C. After 30 min the pellet was thawed on ice, resuspended in 3 ml of Sonication buffer per gram of cells and sonicated on ice. The sonicated cell extract was centrifuged at 16,000 rpm for 1 hour. 1 ul of each extract was mixed with 49 ul of a DNA mixture containing, 12 ul pBR322 (12 ug), 90 ul 10X NEBuffer 2, 22.5 ul PstI (20 U/ul), brought up to 900 ul with water. 25 ul from this tube was mixed with 25 ul of the DNA mixture, a 1:1 dilution. 3 other successive 1:1 dilutions were performed. The reactions were incubated at 37° C. for 1 hour. The entire 25 ul reaction was run on a 0.7% agarose gel. The titers from the crude cell extracts were compared to the known titer from the purified SphI restriction endonuclease. 1 to the 6 clones had little or no detectable SphI restriction endonuclease activity. However, 5 clones had too high a SphI restriction endonuclease activity to be titered accurately in this assay, however it was estimated that the enzyme titer was over $10^5$ units/g of cells. Further titrations put the titer of SphI restriction endonuclease activity around $1.5 \times 10^7$ to $3 \times 10^7$. This level is about $1,000 \times$ more SphI restriction endonuclease activity per gram of cells than is observed in crude extracts of Streptomyces phaeochromogenes. One of these clones selected for further characterization and optimization was given a strain designation of NEB# 808, with the plasmid named pEGsph50-2. A sample of NEB# 808 was deposited at The American Type Culture Collection at Rockville, Md. on Aug. 5, 1992 accession No. 69045. A titration of the SphI restriction endonuclease activity produced from crude extracts of NEB# 808 ATCC Designation No. 690 is shown in FIG. 5.

18. The SphI restriction endonuclease may be produced from NEB# 808 by propagation to mid-log phase in a fermenter containing rich medium with ampicillin and kanamycin. The culture is then induced by the addition of IPTG to a final concentration of 1 mM and allowed to continue growing for 1 to 2 hours. The cells are then harvested by centrifugation.

19. Purification of the SphI restriction endonuclease from NEB# 808: All The following procedures were performed either on ice or at 4° C. 97 grams of cells were resuspended in 291 ml of Buffer A (20 mM potassium phosphate pH 6.9, 0.1 mM EDTA, 1 mM $\beta$-mercaptoethanol, 5% glycerol) containing 0.2M NaCl and broken by passing once through a French press at 11,500 PSIG. The extract was centrifuged at 12,000 rpm for 90 min at 4° C. and the resulting supernatant was passed through a column of DEAE Sepharose CL-6B (5×10 cm) equilibrated with Buffer A containing 0.2M NaCl. The flow-through was collected, diluted 1:1 with buffer A, and applied to a column of Heparin Sepharose CL-6B (5×8 cm) equilibrated with Buffer A containing 0.1M NaCl. The column was washed with 350 ml of Buffer A containing 0.1M NaCl followed by a linear gradient of sodium chloride formed with 800 ml of Buffer A with 0.1M NaCl and 800 ml of Buffer A containing 1M NaCl. Fractions were collected at a flow rate of 5 ml/min. The peak of enzyme activity was pooled and eluted from the column between 0.55–0.75M NaCl. After dialysis against Buffer A with 50 mM NaCl overnight, the pooled enzyme was loaded onto a Mono Q ® HR 10/10 (8 ml) column equilibrated with Buffer A with 50 mM NaCl. Fractions were collected at a flow rate of 1.0 ml/min. The peak of enzyme activity was pooled and eluted from the column between 0.3–0.35M NaCl. The pool was diluted with Buffer A to a NaCl concentration of 50 mM and loaded onto a TSK-Heparin TosoHaas 5PW column (7.5 cm×7.5 mm ID). Fractions were collected at a flow rate of 1.0 ml/min. The peak of enzyme activity eluted from the column between 0.42–0.5M NaCl. Fractions containing activity were pooled and concentrated by dialyzing against Buffer B (10 mM Tris pH 7.4, 50 mM sodium chloride, 0.1 mM EDTA, 1 mM DTT, 50% glycerol. This purification scheme produced $10.8 \times 10^6$ total units of enzyme, a 1% yield.

The SphI restriction endonuclease obtained from this purification was substantially pure and free of non-specific endonuclease and exonuclease. The purity of the SphI restriction endonuclease preparation was checked by looking at the following criteria: 1) Ligation: After a 20-fold overdigestion of $\lambda$ DNA, greater than 95% of the DNA fragments produced were ligated with T4 DNA Ligase (at a 5' termini concentration of 1–2 uM at 16° C.). Of these ligated fragments, 95% were able to be recut. 2) Prolonged digestion: After incubating a 50 ul reaction containing 1 ug of $\lambda$ DNA and 10 units of enzyme for 16 hours, the same pattern of DNA bands was produced as a reaction performed in one hour with one unit of enzyme. 3) Exonuclease Activity: After incubation of 3,000 units of enzyme for 4 hours at 37° C. in a 50 ul reaction containing 1 ug sonicated $^3$H DNA ($10^5$ cpm/ug) less than 0.01% radioactivity was released. 4) Endonuclease Contamination: After incubation of 150 units of enzyme for 4 hours at 37° C. in a 50 ul reaction containing 1 ug $\phi$X174 RFI DNA, less than 25% was converted to RF II. All tests were performed in the following reaction buffer: 50 mM NaCl, 10 mM Tris-HCl, 10 mM MgCl$_2$, 1 mM DTT (pH 7.9 at 25° C.).

What is claimed is:

1. Isolated DNA coding for SphI restriction endonuclease, wherein the isolated DNA is obtainable from the plasmid pEGsph50-2.

2. A recombinant vector comprising a vector into which DNA coding for SphI restriction endonuclease has been inserted.

3. A recombinant vector comprising the isolated DNA of claim 1.

4. The recombinant vector of claim 3, wherein the vector comprises the plasmid pEGsph50-2.

5. A host cell transformed with the recombinant vector of claim 2, 3 or 4.

6. A method of producing SphI restriction endonuclease comprising culturing a host cell transformed with the vector of claim 2, 3 or 4 under conditions suitable for expression of said endonuclease.

7. The isolated DNA of claim 1, wherein the isolated DNA comprises SEQ ID NO:2.

* * * * *

UNITED STATES PATENT AND TRADEMARK OFFICE
CERTIFICATE OF CORRECTION

PATENT NO.  : 5,262,318
DATED       : November 16, 1993
INVENTOR(S) : Ellen P. Guthrie It is certified that error appears in the above-indentified patent and that said Letters Patent is hereby corrected as shown below:

In the Drawings, sheet 3 of 5, figure 3, replace drawing with the attached sheet.

Signed and Sealed this

Seventh Day of June, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,262,318
DATED : November 16, 1993
INVENTOR(S) : Ellen P. Guthrie

Page 2 of 2

It is certified that error appears in the above-indentified patent and that said Letters Patent is hereby corrected as shown below:

"  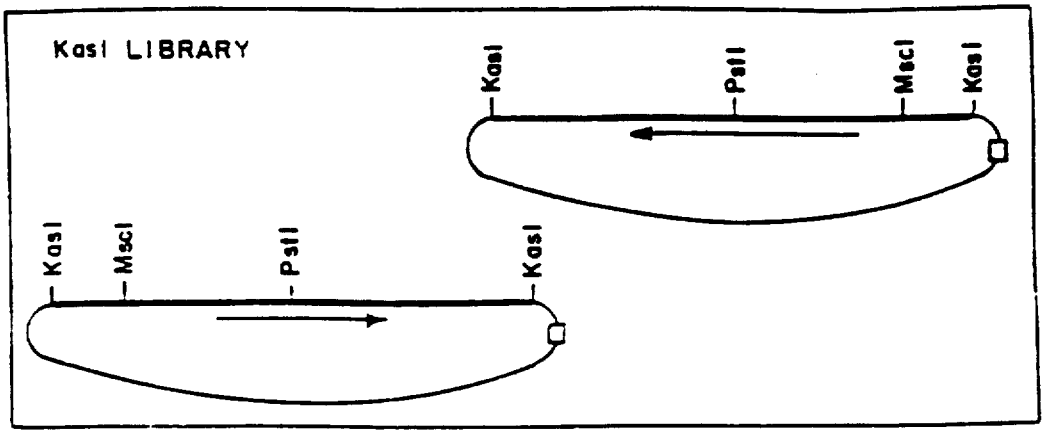  "

with

--  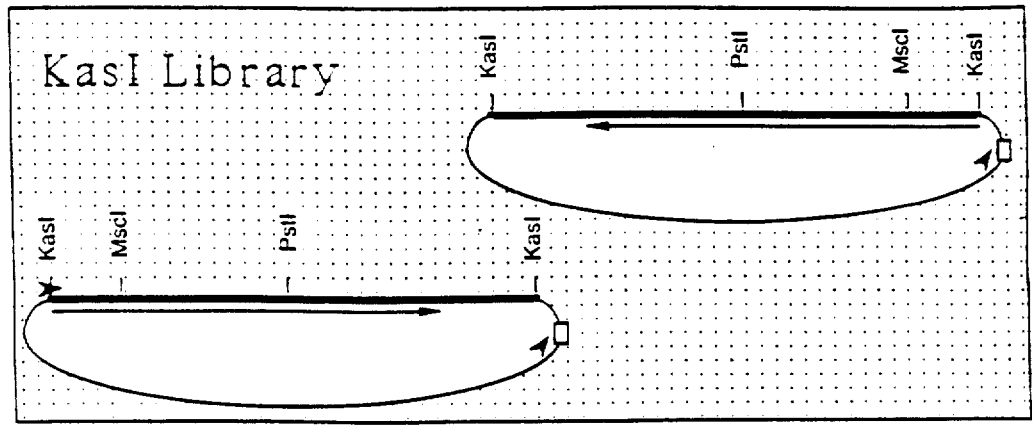  --